United States Patent
Borglin et al.

(10) Patent No.: US 10,925,714 B2
(45) Date of Patent: Feb. 23, 2021

(54) VARIABLE PERMEABILITY LAYERED STRUCTURE AND METHOD

(71) Applicant: Medtronic Vascular, Inc., Santa Rosa, CA (US)

(72) Inventors: Zachary Borglin, San Francisco, CA (US); Keith Perkins, Santa Rosa, CA (US); Julie Benton, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 162 days.

(21) Appl. No.: 16/156,271

(22) Filed: Oct. 10, 2018

(65) Prior Publication Data

US 2019/0159885 A1    May 30, 2019

Related U.S. Application Data

(60) Provisional application No. 62/591,601, filed on Nov. 28, 2017.

(51) Int. Cl.
*A61F 2/07*    (2013.01)
*D02G 3/36*    (2006.01)
(Continued)

(52) U.S. Cl.
CPC .............. *A61F 2/07* (2013.01); *A61F 2/0077* (2013.01); *A61F 2/06* (2013.01); *A61L 27/18* (2013.01);
(Continued)

(58) Field of Classification Search
CPC ........ A61F 2/07; A61F 2002/077; A61F 2/06; A61F 2/0077–2002/0086;
(Continued)

(56) References Cited

U.S. PATENT DOCUMENTS 7,788,952 B2 * 9/2010 Morrison ........... A41D 13/0025
66/195
9,486,346 B2   11/2016 Argentine
(Continued)

FOREIGN PATENT DOCUMENTS

EP    0144534 A2    6/1985
EP    0397500 B1    2/1995
(Continued)

OTHER PUBLICATIONS

U.S. Appl. No. 62/591,601, titled "Advanced Graft Materials for Endovascular Applications", filed Nov. 28, 2017.
(Continued)

*Primary Examiner* — Paul B Prebilic
(74) *Attorney, Agent, or Firm* — Innovation Counsel LLP

(57) ABSTRACT

The techniques of this disclosure generally relate to a variable permeability layered prosthesis including an impermeable outer layer and a permeable inner layer. The impermeable outer layer is well suited to seal a dissection opening of a dissection. The permeable inner layer allows fluid to enter into a dead space between the impermeable outer layer and the permeable inner layer. The fluid in the dead space coagulates in the dead space providing a media for tissue growth into the prosthesis. The ability of tissue to integrate into the prosthesis provides biological fixation of the prosthesis in vessels and prevents endoleaks and migration of the prosthesis.

18 Claims, 5 Drawing Sheets

(51) Int. Cl.

| | |
|---|---|
| A61L 27/58 | (2006.01) |
| D03D 1/00 | (2006.01) |
| D03D 15/00 | (2021.01) |
| A61F 2/06 | (2013.01) |
| D02G 3/44 | (2006.01) |
| A61F 2/00 | (2006.01) |
| A61L 27/18 | (2006.01) |
| A61L 27/54 | (2006.01) |
| A61L 27/56 | (2006.01) |
| A61L 31/14 | (2006.01) |
| A61L 31/16 | (2006.01) |
| A61L 31/02 | (2006.01) |
| A61L 31/06 | (2006.01) |
| A61L 31/10 | (2006.01) |
| B23K 26/388 | (2014.01) |
| A61L 31/04 | (2006.01) |

(52) U.S. Cl.
CPC .............. *A61L 27/54* (2013.01); *A61L 27/56* (2013.01); *A61L 27/58* (2013.01); *A61L 31/022* (2013.01); *A61L 31/06* (2013.01); *A61L 31/10* (2013.01); *A61L 31/148* (2013.01); *A61L 31/16* (2013.01); *D02G 3/36* (2013.01); *D02G 3/448* (2013.01); *D03D 1/00* (2013.01); *D03D 15/0027* (2013.01); *D03D 15/0094* (2013.01); *A61F 2002/0081* (2013.01); *A61F 2002/065* (2013.01); *A61F 2002/075* (2013.01); *A61F 2002/077* (2013.01); *A61F 2210/0004* (2013.01); *A61F 2210/0014* (2013.01); *A61F 2210/0057* (2013.01); *A61F 2210/0071* (2013.01); *A61F 2210/0076* (2013.01); *A61F 2220/0075* (2013.01); *A61F 2230/0069* (2013.01); *A61F 2240/001* (2013.01); *A61F 2250/0003* (2013.01); *A61F 2250/003* (2013.01); *A61F 2250/0023* (2013.01); *A61F 2250/0024* (2013.01); *A61F 2250/0031* (2013.01); *A61F 2250/0051* (2013.01); *A61F 2250/0067* (2013.01); *A61F 2250/0068* (2013.01); *A61F 2250/0069* (2013.01); *A61F 2250/0076* (2013.01); *A61L 31/043* (2013.01); *A61L 2300/258* (2013.01); *A61L 2300/404* (2013.01); *A61L 2300/41* (2013.01); *A61L 2300/412* (2013.01); *A61L 2300/42* (2013.01); *A61L 2420/02* (2013.01); *A61L 2420/08* (2013.01); *B23K 26/388* (2013.01); *D10B 2101/20* (2013.01); *D10B 2331/04* (2013.01); *D10B 2509/06* (2013.01)

(58) Field of Classification Search
CPC ...... A61F 2210/0076; A61F 2210/0004; A61F 2220/0075; A61F 2230/0069; A61F 2250/0003; A61F 2250/0023; A61F 2250/001; A61F 2250/0024; A61F 2250/003; A61F 2250/0031; A61F 2250/0051; A61F 2250/0069; A61L 27/56–27/58; A61L 31/148; A61L 2400/04; A61L 2430/06

See application file for complete search history.

(56) References Cited

U.S. PATENT DOCUMENTS

| | | | |
|---|---|---|---|
| 10,849,731 B2 * | 12/2020 | Cully | .................. C12N 5/0012 |
| 2004/0098096 A1 * | 5/2004 | Eton | ........................ A61F 2/07 |
| | | | 623/1.13 |
| 2005/0220848 A1 | 10/2005 | Bates | |
| 2007/0282160 A1 | 12/2007 | Sheu et al. | |
| 2008/0188923 A1 | 8/2008 | Chu | |
| 2009/0043330 A1 | 2/2009 | To | |
| 2013/0267137 A1 | 10/2013 | Peniston et al. | |
| 2017/0231749 A1 | 8/2017 | Perkins et al. | |
| 2017/0360993 A1 | 12/2017 | Argentine et al. | |

FOREIGN PATENT DOCUMENTS

| | | |
|---|---|---|
| EP | 1820889 B1 | 3/2009 |
| WO | 2000047135 A1 | 8/2000 |
| WO | 2004037116 A2 | 5/2004 |
| WO | 2011103141 A1 | 8/2011 |
| WO | 2013097841 A1 | 7/2013 |
| WO | 2013128718 A1 | 9/2013 |
| WO | 2014133798 A1 | 9/2014 |
| WO | 2017079659 A1 | 11/2016 |

OTHER PUBLICATIONS

U.S. Appl. No. 15/950,612, titled "Graft Materail Having Selectively Advanced Permeability Structure and Method", filed Apr. 11, 2018.
U.S. Appl. No. 16/142,545, titled "Armored Graft Material Structure and Method", filed Sep. 26, 2018.
U.S. Appl. No. 16/143,932, titled "Graft Material Having Heated Puncture Structure and Method", filed Sep. 27, 2018.
U.S. Appl. No. 16/144,078, titled "Biodegradable Composite Yarn Structure and Method", filed Sep. 27, 2018.
U.S. Appl. No. 16/143,125, titled "Framed Biodegradable Yarn Structure and Method", filed Sep. 26, 2018.
PCT/US2018/062482, the International Search Report and the Written Opinion of the Int'l Searching Authority, dated Mar. 27, 2019, 14 pages.
PCT/US2018/062512, the International Search Report and the Written Opinion of the Int'l Searching Authority, dated Apr. 17, 2019, 12 pages.
PCT/US2018/062516, the International Search Report and the Written Opinion of the Int'l Searching Authority, dated Mar. 27, 2019, 13 pages.
PCT/US2018/062549, the International Search Report and the Written Opinion of the Int'l Searching Authority, dated Mar. 28, 2019, 13 pages.
PCT/US2018/062581, the International Search Report and the Written Opinion of the Int'l Searching Authority, dated Mar. 27, 2019, 15 pages.
PCT/US2018/062589, the International Search Report and the Written Opinion of the Int'l Searching Authority, dated Mar. 27, 2019, 13 pages.

* cited by examiner

VARIABLE PERMEABILITY LAYERED STRUCTURE AND METHOD

CROSS-REFERENCE TO RELATED APPLICATIONS

This application claims the benefit of U.S. Provisional Application No. 62/591,601, filed on Nov. 28, 2017, entitled "ADVANCED GRAFT MATERIALS FOR ENDOVASCULAR APPLICATIONS" of Borglin et al., which is incorporated herein by reference in its entirety.

FIELD

The present technology is generally related to an intra-vascular device and method. More particularly, the present application relates to a device for treatment of intra-vascular diseases.

BACKGROUND

A conventional stent-graft typically includes a radially expandable reinforcement structure, formed from a plurality of annular stent rings, and a cylindrically shaped layer of graft material defining a lumen to which the stent rings are coupled. Stent-grafts are well known for use in tubular shaped human vessels.

To illustrate, endovascular aneurysmal exclusion is a method of using a stent-graft to exclude pressurized fluid flow from the interior of an aneurysm, thereby reducing the risk of rupture of the aneurysm and the associated invasive surgical intervention. The graft material of traditional stent-grafts is extremely hydrophobic and presents a hostile environment for the recruitment and proliferation of cells. The inability of tissue to integrate into the graft material prevents the biological fixation of the stent-graft in vessels and makes the stent-graft susceptible to endoleaks and migration.

SUMMARY

The techniques of this disclosure generally relate to a variable permeability layered prosthesis including an impermeable outer layer and a permeable inner layer. The impermeable outer layer is well suited to seal a dissection opening of a dissection. The permeable inner layer allows fluid to enter into a dead space between the impermeable outer layer and the permeable inner layer. The fluid in the dead space coagulates in the dead space providing a media for tissue growth into the prosthesis. The ability of tissue to integrate into the prosthesis provides biological fixation of the prosthesis in vessels and prevents endoleaks and migration of the prosthesis.

In one aspect, the present disclosure provides a prosthesis having a variable permeability layered graft material including a permeable inner layer, an impermeable outer layer, and crosslink yarns attaching the permeable inner layer to the impermeable outer layer.

In another aspect, the disclosure provides a prosthesis having a variable permeability layered graft material including a permeable inner layer comprising an inner surface and an outer surface and an impermeable outer layer comprising an inner surface and an outer surface. A dead space exists between the outer surface of the permeable inner layer and the inner surface of the impermeable outer layer when the prosthesis is in a deployed configuration.

In yet another aspect, the disclosure provides a method including deploying a prosthesis within a vessel, the prosthesis comprising a permeable inner layer and an impermeable outer layer. Fluid passes through the permeable inner layer and into a dead space between the permeable inner layer and the impermeable outer layer. The fluid coagulates in the dead space.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
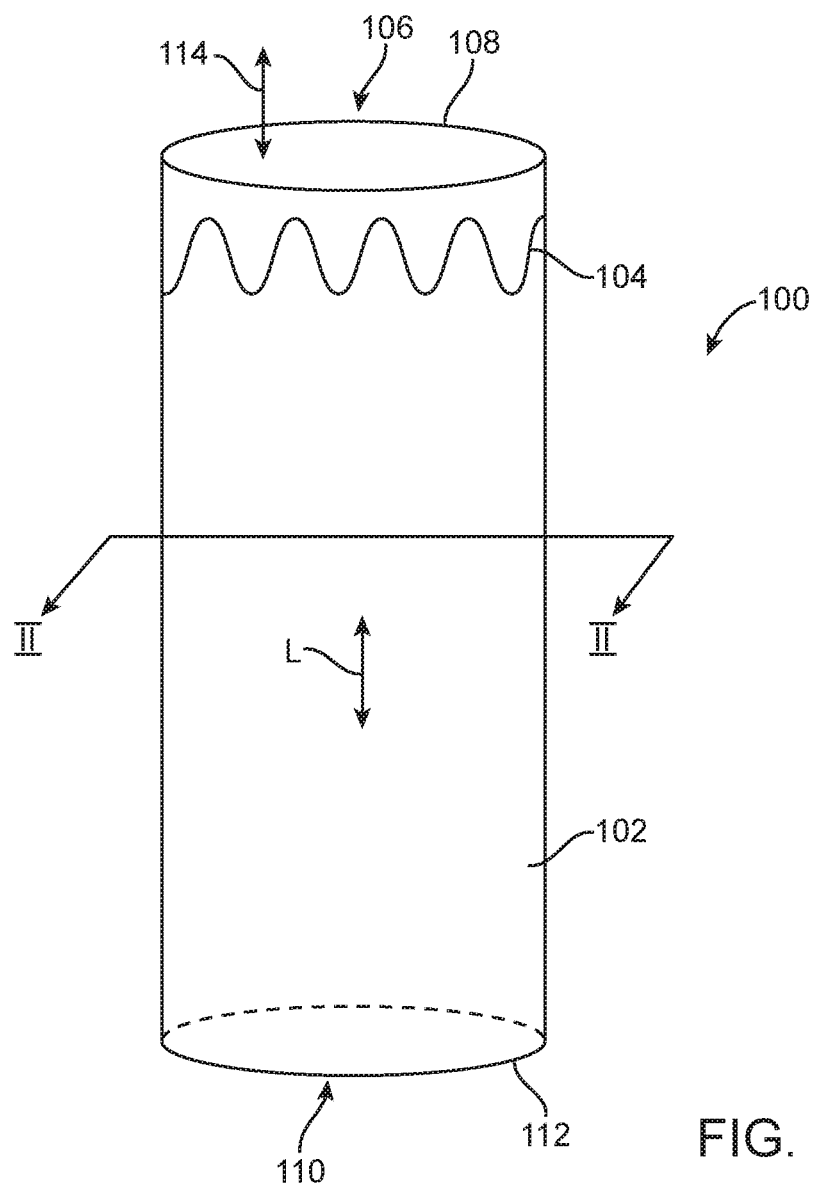
FIG. 1 is a perspective view of a variable permeability layered stent-graft in accordance with one embodiment.

FIG. 1 is a perspective view of a variable permeability layered stent-graft 100 in accordance with one embodiment. Referring now to FIG. 1, stent-graft 100, sometimes called a prosthesis, includes a variable permeability layered graft material 102 and one or more stent rings 104 coupled to graft material 102. Illustratively, stent rings 104 are self-expanding stent rings, e.g., nickel titanium alloy (NiTi), sometimes called Nitinol, or self-expanding members. The inclusion of stent rings 104 is optional and in one embodiment stent rings 104 are not included. In another embodiment, stent rings 104 are balloon expandable stents.

In accordance with this embodiment, graft material 102 includes a proximal opening 106 at a proximal end 108 of graft material 102 and a distal opening 110 at a distal end 112 of graft material 102.

Further, stent-graft 100 includes a longitudinal axis L. A lumen 114 is defined by graft material 102, and generally by stent-graft 100. Lumen 114 extends generally parallel to longitudinal axis L and between proximal opening 106 and distal opening 110 of stent-graft 100.

As used herein, the proximal end of a prosthesis such as stent-graft 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of stent-graft 100 is the end nearest the operator (the end nearest the handle), i.e., the distal end of the catheter and the proximal end of stent-graft 100 are the ends furthest from the handle while the proximal end of the catheter and the distal end of stent-graft 100 are the ends nearest the handle. However, those of skill in the art will understand that depending upon the access location, stent-graft 100 and the delivery system descriptions may be consistent or opposite in actual usage.

Graft material 102 is cylindrical having a substantially uniform diameter. However, in other embodiments, graft material 102 varies in diameter, is bifurcated at distal end 112, and/or is a multi-limbed device for branching applications.

Figure 2:
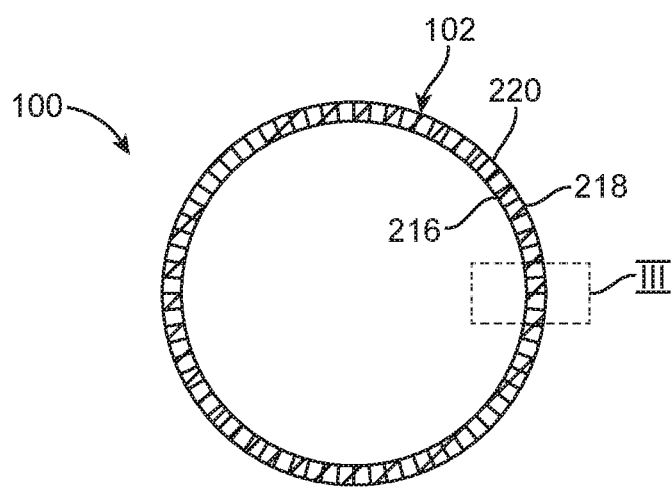
FIG. 2 is a cross-sectional view of the stent-graft of FIG. 1 along the line II-II in accordance with one embodiment.
Figure 3:
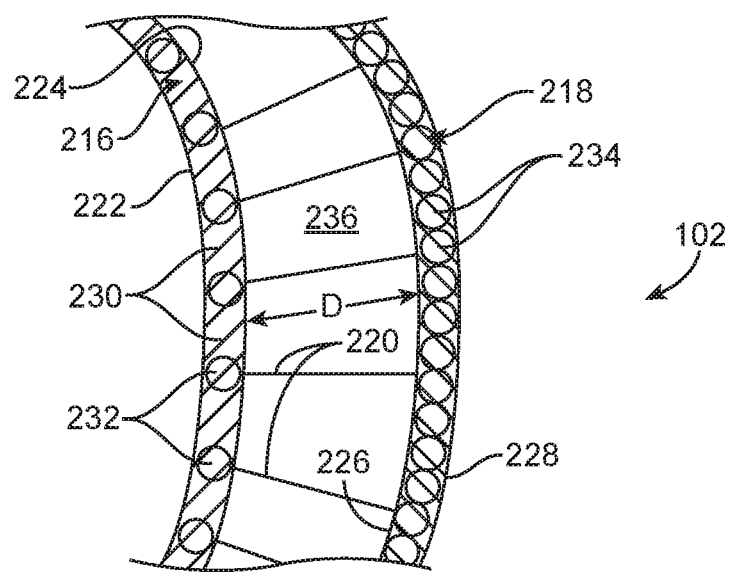
FIG. 3 is an enlarged view of a region III of the stent-graft of FIG. 2 in a deployed configuration in accordance with one embodiment.

FIG. 2 is a cross-sectional view of stent-graft 100 of FIG. 1 along the line II-II in accordance with one embodiment. FIG. 3 is an enlarged view of a region III of stent-graft 100 of FIG. 2 in a deployed configuration in accordance with one embodiment.

Referring now to FIGS. 1-3 together, graft material 102 includes a permeable inner layer 216, an impermeable outer layer 218, and crosslink yarns 220. Permeable inner layer 216 includes an inner surface 222 and an opposite outer surface 224, e.g., cylindrical surfaces in accordance with this embodiment. Impermeable outer layer 218 includes an inner surface 226 and an opposite outer surface 228, e.g., cylindrical surfaces in accordance with this embodiment.

Permeable inner layer 216 is permeable to fluid, e.g., blood. As used herein, permeable means having pores or openings that permit fluid, e.g., blood, to pass through.

Generally, permeable inner layer 216 includes a plurality of openings 230, sometimes called pores, extending between inner surface 222 and outer surface 224. Openings 230 are sufficiently large such that fluid can readily pass, e.g., leak, through permeable inner layer 216, e.g., from inner surface 222 to outer surface 224. However, openings are sufficiently small to prevent free flow of fluid though permeable inner layer 216.

In one embodiment, the porosity of permeable inner layer 216 is engineered to clot slowly becoming impermeable over time. In accordance with this embodiment, permeable inner layer 216 is acutely permeable but becomes impermeable over time thus trapping blood as discussed further below.

In one embodiment, permeable inner layer 216 is formed of yarns 232 which are loosely woven, knitted, sewn, or otherwise combined to create permeable inner layer 216. Openings 230 are spaces between yarns 232 and are arranged in a regular spaced array in one embodiment. In one embodiment, permeable inner layer 216 is polyester terephthalate (PET), ePET, or other graft material or textile.

In contrast, impermeable outer layer 218 is impermeable to fluid, e.g., blood. Generally, impermeable outer layer 218 is less permeable than permeable layer 216. Impermeable outer layer 218 has an absence of openings extending between inner surface 226 and outer surface 228. In one embodiment, impermeable outer layer 218 is formed of yarns 234 which are tightly woven, knitted, sewn, or otherwise combined to create impermeable outer layer 218 although is a single sheet in accordance with another embodiment.

In one embodiment, impermeable outer layer 218 is polyester terephthalate (PET), ePET, or other graft material or textile. In accordance with this embodiment, impermeable outer layer 218 is persistent, e.g., will last in the human body for ten years or more. Accordingly, impermeable outer layer 218 is impermeable when initially deployed, sometime referred to as having acute impermeability, and maintains the impermeability over time, sometimes referred to as having persistent impermeability.

However, in another embodiment, impermeable outer layer 218 has acute impermeability, and degrades, e.g., biodegrades, over time to have permeability to encourage tissue ingrowth therein. In various embodiments, impermeable outer layer 218 includes an acutely impermeable material that biodegrades over time, e.g., includes a biodegradable material, as set forth in: Borglin et al., U.S. patent application Ser. No. 15/950,612, filed on Apr. 11, 2018, entitled "GRAFT MATERIAL HAVING SELECTIVELY ADVANCED PERMEABILITY STRUCTURE AND METHOD"; Perkins et al., U.S. patent application Ser. No. 16/142,545, filed on Sep. 26, 2018, entitled "ARMORED GRAFT MATERIAL STRUCTURE AND METHOD"; Borglin et al., U.S. patent application Ser. No. 16/143,932, filed on Sep. 27, 2018, entitled "GRAFT MATERIAL HAVING HEATED PUNCTURE STRUCTURE AND METHOD"; Perkins et al., U.S. patent application Ser. No. 16/144,078, filed on Sep. 27, 2018, entitled "BIODEGRADABLE COMPOSITE YARN STRUCTURE AND METHOD"; Perkins et al., U.S. patent application Ser. No. 16/143,125, filed on Sep. 26, 2018, entitled "FRAMED BIODEGRADABLE YARN STRUCTURE AND METHOD", which are all herein incorporated by reference in their entirety.

Inner surface 222 of permeable inner layer 216 is generally inner surface 222 of graft material 102. Inner surface 222 defines lumen 114 and is sometimes called a luminal surface 222 of graft material 102.

Outer surface 228 of impermeable outer layer 218 is generally outer surface 228 of graft material 102. Outer surface 228 is sometimes called an abluminal surface 228 of graft material 102.

Outer surface 224 of permeable inner layer 216 is spaced apart from and faces inner surface 226 of impermeable outer layer 218. A dead space 236 exists between permeable inner layer 216 and impermeable outer layer 218. More particularly, dead space 236 exists between outer surface 224 of permeable inner layer 216 and inner surface 226 of impermeable outer layer 218.

Crosslink yarns 220 extend across dead space 236 between permeable inner layer 216 and impermeable outer layer 218. In one embodiment, crosslink yarns 220 extend radially outward from permeable inner layer 216 to impermeable outer layer 218 although can extend non-radially in other embodiments. Generally, crosslink yarns 220 attach and set the relative distance between permeable inner layer 216 and impermeable outer layer 218. In one embodiment, crosslink yarns 220 are long string like members, sometimes called threads, fibers, filaments, or cylindrical structures, that are laced or passed through permeable inner layer 216 and impermeable outer layer 218.

Although graft material 102 including permeable inner layer 216, impermeable outer layer 218, and crosslink yarns 220 is set forth, in other embodiments, a vast variety of different textile spacers are employed, such as a spacer knit. The permeability of each of permeable inner layer 216, impermeable outer layer 218, and crosslink yarns 220 can be independently changed to promote and control flow. Each of permeable inner layer 216, impermeable outer layer 218, and crosslink yarns 220 are made of varied material in various embodiments.

Figure 4:
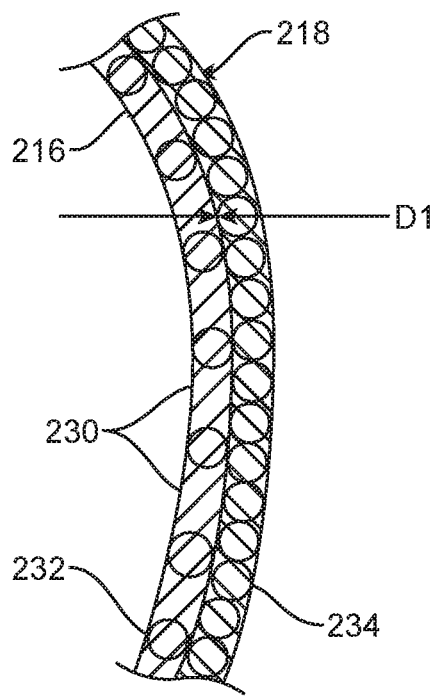
FIG. 4 is an enlarged view of the region III of the stent-graft of FIG. 2 in a predeployment configuration in accordance with one embodiment.

FIG. 3 illustrates graft material 102 in a deployed configuration where dead space 236 exists between permeable inner layer 216 and impermeable outer layer 218. FIG. 4 is an enlarged view of the region III of stent-graft 100 of FIG. 2 in a predeployment configuration in accordance with one embodiment.

Referring to FIGS. 3 and 4 together, in the predeployment configuration as illustrated in FIG. 4, crosslink yarns 220 are collapsed and compressed between permeable inner layer 216 and impermeable outer layer 218. For example, permeable inner layer 216 and impermeable outer layer 218 are collapsed to be in abutting contact and loaded into the delivery catheter. In the collapsed state, stent-graft 100 is sometimes said to be in a predeployment configuration. By collapsing permeable inner layer 216 and impermeable outer layer 218 and eliminating dead space 236, the delivery profile of stent-graft 100 is minimized. Stated another way, stent-graft 100 has a low profile and a low loading force when in the predeployment configuration.

In one embodiment, crosslink yarns 220 are chosen to hold permeable inner layer 216 and impermeable outer layer 218 tightly together until the body environment causes crosslink yarns 220 to relax. In one embodiment, crosslink yarns 220 relax through the breaking of cross linkages in a polymer structure of crosslink yarns 220. Generally, a distance D as illustrated in FIG. 3 between permeable inner layer 216 and impermeable outer layer 218 is greater when crosslink yarns 220 are relaxed than a distance D1 as illustrated in FIG. 4 between permeable inner layer 216 and impermeable outer layer 218 when stent-graft 100 in in the predeployment configuration and crosslink yarns 220 are not relaxed, e.g., compressed.

Once released from the predeployment configuration as illustrated in FIG. 4, e.g., by removal of the delivery sheath, cross-link yarns 220 relax and return to the unconstrained and relaxed configuration as illustrate in FIG. 3 and discussed above. More particularly, upon being released, cross-link yarns 220 relax and separate, i.e., move, permeable inner layer 216 from impermeable outer layer 218 thereby creating dead space 236.

Figure 6:
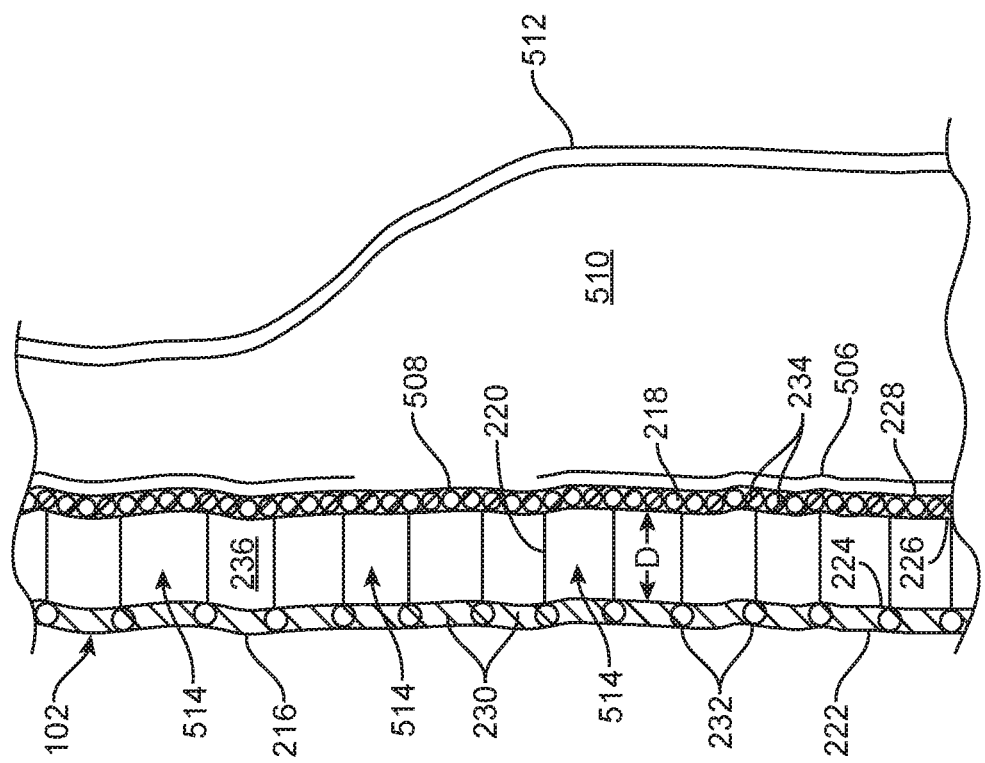
FIG. 6 is an enlarged cross-sectional view of a region VI of the vessel assembly of FIG. 5 in accordance with one embodiment.
Figure 5:
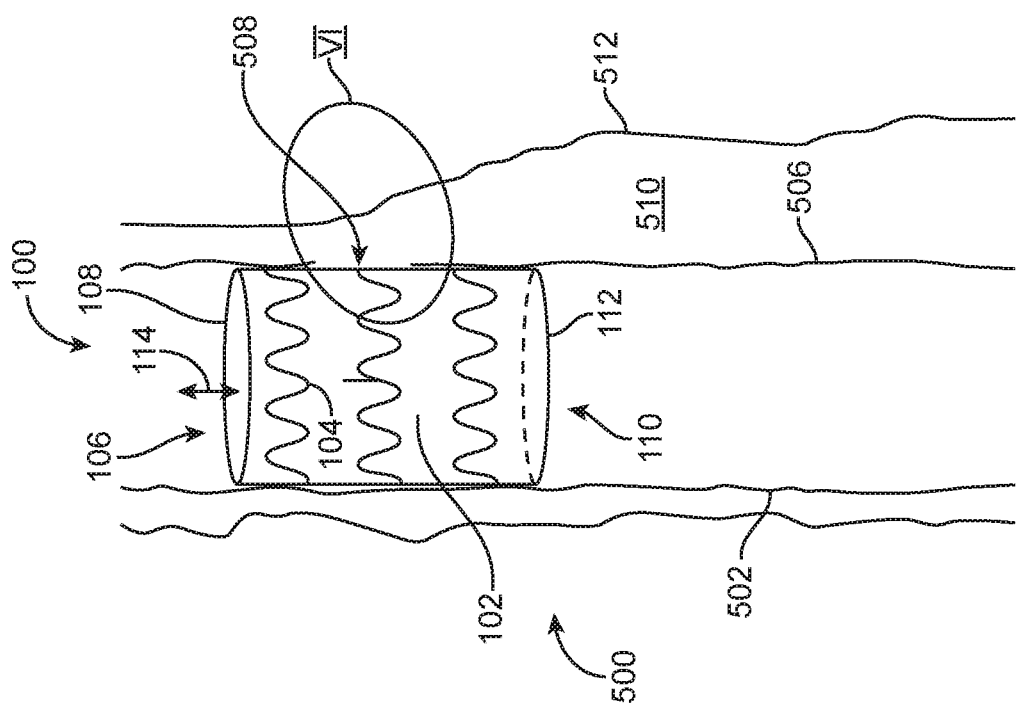
FIG. 5 is a cross-sectional view of a vessel assembly including the stent-graft of FIG. 1 after initial deployment within a vessel having a dissection in accordance with one embodiment.

FIG. 5 is a cross-sectional view of a vessel assembly 500 including stent-graft 100 of FIG. 1 after initial deployment within a vessel 502 having a dissection in accordance with one embodiment. FIG. 6 is an enlarged cross-sectional view of a region VI of vessel assembly 500 of FIG. 5 in accordance with one embodiment.

Referring to FIGS. 1, 5-6 together, a dissection is a condition in which an inner layer 506 of vessel 502 tears to have a dissection opening 508, sometimes called an entry tear. Fluid, e.g., blood, flows through dissection opening 508 and into a false lumen 510 between inner layer 506 and one or more other outer layers 512 of vessel 502. Left untreated, false lumen 510 can rupture outer layers 512 of vessel 502 leading to serious complications and often death.

In accordance with this embodiment, stent-graft 100 is deployed to cover and exclude dissection opening 508. As discussed above, when initially deployed, impermeable outer layer 218 is impermeable thus sealing dissection opening 508 and preventing pressurized fluid flow through false lumen 510. Outer surface 228 of impermeable outer layer 218 contacts vessel 502. Stent-graft 100 is held to dissection opening 508 by stent ring(s) 104 and/or surgically sewn to vessel 502 in various embodiments.

At the same time, fluid 514, e.g., blood, flows through permeable inner layer 216 and into dead space 236. More particularly, fluid 514 flows through openings 230 and fills dead space 236. As dead space 236 is completely sealed from the outside by impermeable outer layer 218 and partially sealed by permeable inner layer 216, fluid 514 is stagnant within dead space 236. This causes fluid 514 within dead space 236 to coagulate and disperse within dead space 236 creating media for strong tissue growth as discussed further below.

In one embodiment, permeable inner layer 216 becomes impermeable over time thus trapping fluid 514 in dead space 236. This causes impermeable outer layer 218 to balloon outward to fill and conform to the uneven contours of vessel 502, e.g., a diseased aorta, thus enhancing seal.

In one embodiment, a prothrombogenic material is added to dead space 236 to enhance clot formation and maturation of thrombus in dead space 236 to fibrocellular tissue as discussed further below.

Further, fluid 514 flows through lumen 114 of stent-graft 100. As fluid 514 pulsates, e.g., due to the rhythmic beating of the heart, the pressure of fluid 514 flowing through stent-graft 100 also rhythmically increases and falls.

This pressure change causes permeable inner layer 216 to be compressed towards impermeable outer layer 218 and then released. Stated another way, the distance D between permeable inner layer 216 and impermeable outer layer 218 varies with blood circulation. More generally, cross link yarns 220 are repeatedly compressed and released due to the pulsation of fluid passing through stent-graft 100. In this manner, the pressure change is buffered by permeable inner layer 216 and cross-link yarns 220 reducing the pressure applied to impermeable outer layer 218. This, in turn, reduces motion and wear on impermeable outer layer 218. Accordingly, the lifespan of stent-graft 100 is increased and stent-graft 100 is well suited for younger patient populations, where stent-graft 100 must last for a long time, e.g., greater than 10 years.

Figure 7:
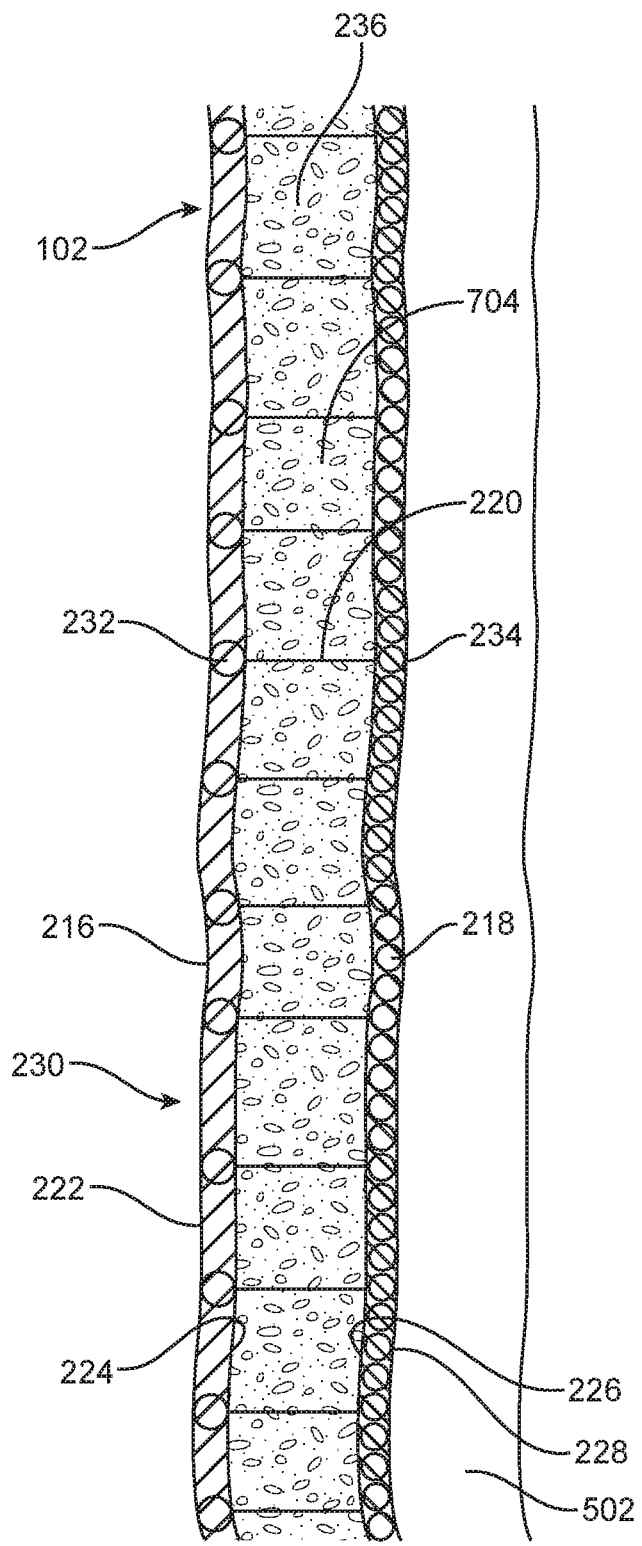
FIG. 7 is a cross-sectional view of the region VI of the vessel assembly of FIG. 5 after a period of time after deployment of the stent-graft within the vessel in accordance with one embodiment.

FIG. 7 is a cross-sectional view of region VI of vessel assembly 500 of FIG. 5 after a period of time after deployment of stent-graft 100 within vessel 502 in accordance with one embodiment. Referring now to FIGS. 1, 5-7, due to the covering and exclusion of the dissection with stent-graft 100, dissection opening 508 heals and closes and false lumen 510 collapses. Dissection opening 508 is sealed with growth of tissue 704 in one embodiment, sometimes called host tissue growth.

In addition, due to the stagnation of fluid within dead space 236, tissue 704 integrates into dead space 236. In various embodiments as discussed above, impermeable outer layer 218 biodegrades allowing tissue 704 to encase impermeable outer layer 218. In one embodiment, tissue 704 integrates into dead space 236 in a short period of time, e.g., less than one year.

By sealing dissection opening 508 with host tissue 704, a highly durable and long-lasting solution is implemented enabling younger patients to receive therapy with stent-graft 100. Further, by providing the ability of tissue 704 to integrate into the stent-graft 100, biological fixation of stent-graft 100 in vessels is provided and endoleaks and migration of stent-graft 100 is avoided.

In one embodiment, stent ring(s) 104 are designed to break at discrete places at a time point after integration of tissue 704. By having stent ring(s) 104 break over time, vessel 502 is allowed to assume a more natural motion and allowed to change with the native tissue more readily.

Figure 9:
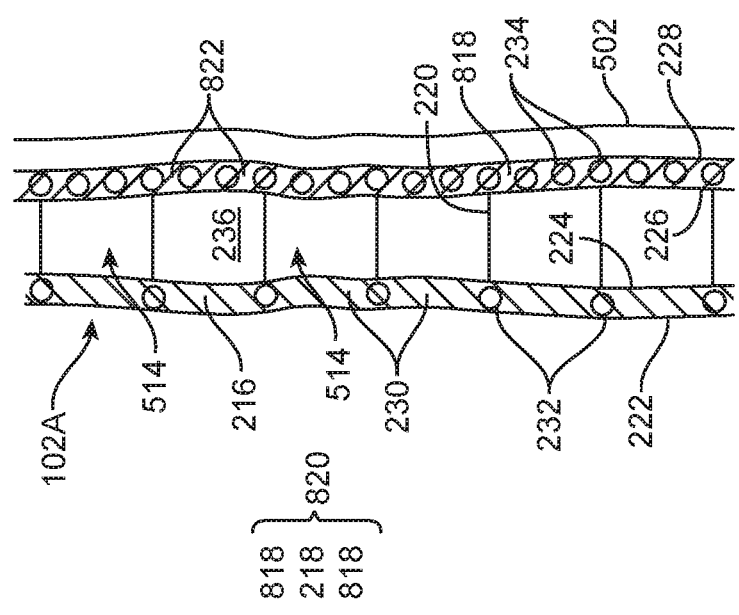
FIG. 9 is an enlarged cross-sectional view of a region IX of the vessel assembly of FIG. 8 in accordance with one embodiment.
Figure 8:
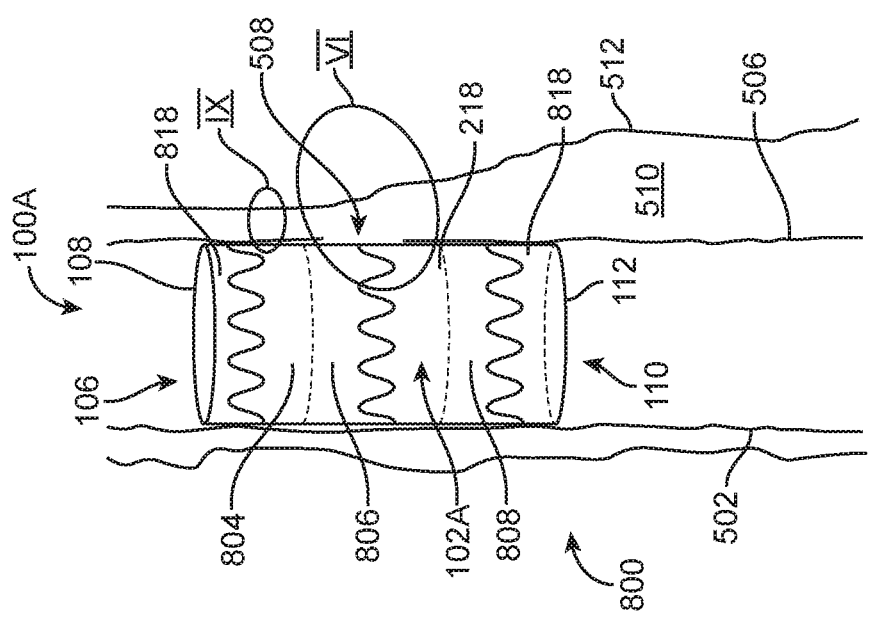
FIG. 8 is a cross-sectional view of a vessel assembly including a stent-graft in accordance with another embodiment.

FIG. 8 is a cross-sectional view of a vessel assembly 800 including a stent-graft 100A in accordance with another embodiment. FIG. 9 is an enlarged cross-sectional view of a region IX of vessel assembly 800 of FIG. 8 in accordance with one embodiment. Stent-graft 100A of FIG. 8 is similar to stent-graft 100 of FIG. 1 and only the significant differences are discussed below. As discussed further below, FIGS. 6 and 7 are representative of a region VI of vessel assembly 500 including stent-graft 100 of FIG. 5 and also of a region VI of vessel assembly 800 including stent-graft 100A of FIG. 8 at initial and later stages of deployment.

In accordance with this embodiment, referring now to FIGS. 6, 8-9 together. a graft material 102A and more generally stent-graft 100A includes at least three zones 804, 806, 808 in accordance with this embodiment. Proximal seal zone 804 extends from proximal end 108 to exclusion zone 806. Exclusion zone 806 extends from proximal seal zone 804 to distal seal zone 808. Distal seal zone 808 extends from exclusion zone 806 to distal end 112.

In accordance with this embodiment, exclusion zone 806 covers and excludes dissection opening 508. Exclusion zone 806 includes permeable inner layer 216, impermeable outer layer 218, and crosslink yarns 220 as discussed above in reference to FIG. 6.

Further, proximal seal zone 804 and distal seal zone 808 directly contact vessel 502. In accordance with this embodiment, instead of impermeable outer layer 218 as in stent-graft 100 as set forth above, in proximal seal zone 804 and distal seal zone 808, a permeable outer layer 818 is used. More particularly, an outer layer 820 of stent-graft 100A includes permeable outer layer 818 in proximal seal zone 804 and distal seal zone 808 and further includes impermeable outer layer 218 in exclusion zone 806. Impermeable outer layer 218 is discussed above in reference to FIGS. 1-7. Outer layer 820 is attached to permeable inner layer 216 by crosslink yarns 220.

Permeable outer layer 818 in accordance with this embodiment is permeable and includes tissue integration openings 822. Generally, permeable outer layer 818 includes a plurality of tissue integration openings 822, sometimes called pores, extending between inner surface 226 and outer surface 228 of permeable outer layer 818.

In one embodiment, permeable outer layer 818 is formed of yarns 234 which are loosely woven, knitted, sewn, or otherwise combined to create permeable outer layer 818.

Tissue integration openings 822 are spaces between yarns 234 and are arranged in a regular spaced array in one embodiment. In one embodiment, permeable outer layer 818 is polyester terephthalate (PET), ePET, or other graft material or textile.

In one embodiment, permeable inner layer 216 has a sufficient permeability to allow fluid, e.g., blood, to pass through permeable inner layer 216 and fill dead space 236. Permeable outer layer 818 has a sufficient permeability to allow tissue integration through permeable outer layer 818. The permeabilities of permeable inner layer 216 and permeable outer layer 818 are different in one embodiment. In another embodiment, the permeabilities of permeable inner layer 216 and permeable outer layer 818 are the same.

Stent-graft 100A is deployed into a vessel 502 to exclude dissection opening 508 using any one of a number of techniques well known to those of skill in the art. More particularly, proximal seal zone 804 and distal seal zone 808 are deployed proximally and distally to dissection opening 508, respectively. Proximal seal zone 804 and distal seal zone 808 directly contact vessel 502.

As discussed above, when initially deployed, impermeable outer layer 218 is impermeable thus sealing dissection opening 508 and preventing pressurized fluid flow through false lumen 510. Outer surface 228 of impermeable outer layer 218 contacts vessel 502 and covers dissection opening 508. Stent-graft 100A is held to dissection opening 508 by stent ring(s) 104 and/or surgically sewn to vessel 502 in various embodiments.

At the same time, fluid 514, e.g., blood, flows through permeable inner layer 216 and into dead space 236. More particularly, fluid 514 flows through openings 230 and fills dead space 236. Dead space 236 is sealed from the outside by impermeable outer layer 218 in exclusion zone 806 or permeable outer layer 818/vessel 502 in proximal seal zone 804 and distal seal zone 808. As further discussed above, dead space 236 is partially sealed from the inside by permeable inner layer 216. Accordingly, fluid 514 is stagnant within dead space 236. This causes fluid 514 within dead space 236 to coagulate and disperse within dead space 236 creating media for strong tissue growth as discussed further below.

Figure 10:
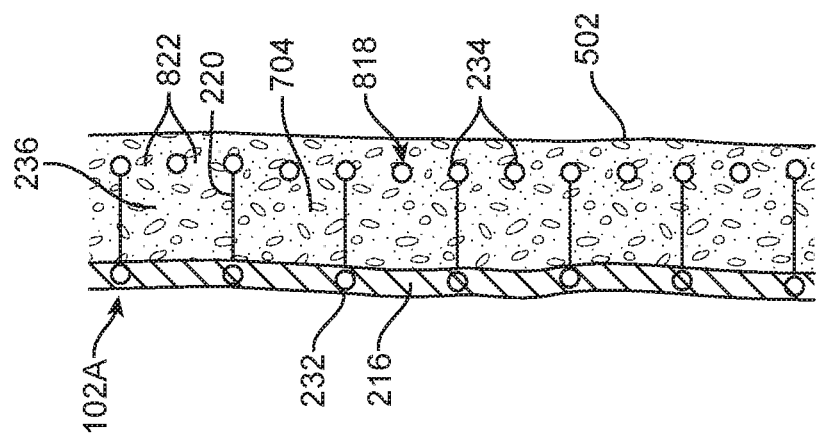
FIG. 10 is a cross-sectional view of the region IX of the vessel assembly of FIG. 8 after a period of time after deployment of the stent-graft within a vessel in accordance with one embodiment.

FIG. 10 is a cross-sectional view of region IX of vessel assembly 800 of FIG. 8 after a period of time after deployment of stent-graft 100A within vessel 502 in accordance with one embodiment. Referring now to FIGS. 1, 7-10, due to the covering and exclusion of the dissection with stent-graft 100A, dissection opening 508 heals and closes and false lumen 510 collapses as illustrated in FIG. 7. Dissection opening 508 is sealed with growth of tissue 704 in one embodiment, sometimes called host tissue growth.

In addition, due to the stagnation of fluid within dead space 236, tissue 704 integrates into dead space 236 as illustrated in FIGS. 7, 10. As permeable outer layer 818 includes tissue integration openings 822, tissue 704 encase permeable outer layer 818 in proximal seal zone 804 and distal seal zone 808 as illustrated in FIG. 10. In one embodiment, tissue 704 integrates into dead space 236 in a short period of time, e.g., less than one year.

By sealing dissection opening 508 with host tissue 704 and encasing permeable outer layer 818 in proximal seal zone 804 and distal seal zone 808 with host tissue 704, a highly durable and long-lasting solution is implemented enabling younger patients to receive therapy with stent-graft 100A. Further, by providing the ability of tissue 704 to integrate into the stent-graft 100A, biological fixation of stent-graft 100A in vessels is provided and endoleaks and migration of stent-graft 100A is avoided.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A prosthesis comprising:
   a variable permeability layered graft material comprising:
   a permeable inner layer;
   an impermeable outer layer; and
   crosslink yarns attaching the permeable inner layer to the impermeable outer layer, wherein a dead space exists between the permeable inner layer and the impermeable outer layer when the crosslink yarns are relaxed, wherein the crosslink yarns hold the permeable inner layer and the impermeable outer layer tightly together when the crosslink yarns are not relaxed.

2. The prosthesis of claim 1 wherein the permeable inner layer comprises openings that are configured to permit fluid to pass through the permeable inner layer.

3. The prosthesis of claim 2 wherein the openings extend from an inner surface of the permeable inner layer to an outer surface of the permeable inner layer.

4. The prosthesis of claim 3 wherein the inner surface of the permeable inner layer defines a lumen.

5. The prosthesis of claim 2 wherein the permeable inner layer comprises yarns, the openings being spaces between the yarns.

6. The prosthesis of claim 1 wherein the impermeable outer layer is impermeable to fluid.

7. The prosthesis of claim 1 wherein the impermeable outer layer is less permeable than the permeable inner layer.

8. The prosthesis of claim 1 wherein the impermeable outer layer comprises a biodegradable material.

9. The prosthesis of claim 8 wherein the impermeable outer layer is configured to be acutely impermeable and to biodegrade to have permeability over time.

10. The prosthesis of claim 1 wherein the dead space exists between the impermeable outer layer and the permeable inner layer when the prosthesis is in a deployed configuration.

11. A prosthesis comprising:
    a variable permeability layered graft material comprising:
    a permeable inner layer comprising an inner surface and an outer surface;
    an impermeable outer layer comprising an inner surface and an outer surface; and
    crosslink yarns,
    wherein the crosslink yarns are relaxed and extend across a dead space existing between the outer surface of the permeable inner layer and the inner surface of the impermeable outer layer when the prosthesis is in a deployed configuration, wherein the crosslink yarns are not relaxed and hold the permeable inner layer and the impermeable outer layer tightly together and the dead space is eliminated when the prosthesis is in a predeployment configuration.

12. The prosthesis of claim 11 wherein a distance exists between the permeable inner layer and the impermeable outer layer when the prosthesis is in the deployed configuration, the distance being set by the crosslink yarns.

13. The prosthesis of claim 11 wherein the crosslink yarns are collapsed and compressed between the permeable inner layer and the impermeable outer layer when the prosthesis is in the predeployment configuration.

14. The prosthesis of claim 11 wherein the permeable inner layer is in abutting contact with the impermeable outer layer when the prosthesis is in the predeployment configuration.

15. The prosthesis of claim 1 wherein the crosslink yarns relax through breaking of cross linkages in a polymer structure of the crosslink yarns.

16. The prosthesis of claim 15 wherein a body environment causes the breaking.

17. The prosthesis of claim 11 wherein the crosslink yarns relax through breaking of cross linkages in a polymer structure of the crosslink yarns.

18. The prosthesis of claim 17 wherein a body environment causes the breaking.

* * * * *